US010415550B2

(12) United States Patent
Chen et al.

(10) Patent No.: US 10,415,550 B2
(45) Date of Patent: Sep. 17, 2019

(54) EVAPORATION-DRIVEN ENGINES

(71) Applicant: THE TRUSTEES OF COLUMBIA UNIVERSITY IN THE CITY OF NEW YORK, New York, NY (US)

(72) Inventors: Xi Chen, New York, NY (US); Davis W. Goodnight, Salisbury, NC (US); Ozgur Sahin, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 1 day.

(21) Appl. No.: 15/308,122

(22) PCT Filed: May 8, 2015

(86) PCT No.: PCT/US2015/029963
§ 371 (c)(1),
(2) Date: Nov. 1, 2016

(87) PCT Pub. No.: WO2015/172067
PCT Pub. Date: Nov. 12, 2015

(65) Prior Publication Data
US 2017/0051728 A1 Feb. 23, 2017

Related U.S. Application Data

(60) Provisional application No. 61/990,372, filed on May 8, 2014.

(51) Int. Cl.
F03G 7/06 (2006.01)
F03G 7/00 (2006.01)
(Continued)

(52) U.S. Cl.
CPC .............. F03G 7/06 (2013.01); B01J 20/22 (2013.01); C12N 1/20 (2013.01); F03G 7/005 (2013.01)

(58) Field of Classification Search
None
See application file for complete search history.

(56) References Cited

U.S. PATENT DOCUMENTS 4,087,971 A * 5/1978 Hart ..................... F03G 7/065
60/527
5,805,381 A 9/1998 Resh
(Continued)

FOREIGN PATENT DOCUMENTS

WO WO 97/08458 A1 3/1997
WO WO 2012071426 A2 * 5/2012 ............... H02N 2/18

OTHER PUBLICATIONS

International Search Report and Written Opinion dated Oct. 5, 2015 in International Application No. PCT/US15/29963.

Primary Examiner — Mark A Laurenzi
Assistant Examiner — Mickey H France
(74) Attorney, Agent, or Firm — Baker Botts L.L.P.

(57) ABSTRACT

Evaporation-driven engines are disclosed herein. An example engine can include a water source having a high humidity zone proximate the surface of the water source, a supporting structure, and a hygroscopic material disposed on the supporting structure and configured to generate mechanical force in response to a changing relative humidity. The hygroscopic material can be repeatedly exposed to the high humidity zone and removed from the high humidity zone thereby causing the hygroscopic material to generate mechanical force.

31 Claims, 15 Drawing Sheets

(51) Int. Cl.
*B01J 20/22* (2006.01)
*C12N 1/20* (2006.01)

(56) References Cited

U.S. PATENT DOCUMENTS

| | | |
|---|---|---|
| 7,385,336 B2 | 6/2008 | Uphoff |
| 2007/0184238 A1* | 8/2007 | Hockaday ................ B32B 7/00 428/98 |
| 2008/0099960 A1 | 5/2008 | Okuzaki |
| 2013/0285386 A1 | 10/2013 | Sahin |

* cited by examiner

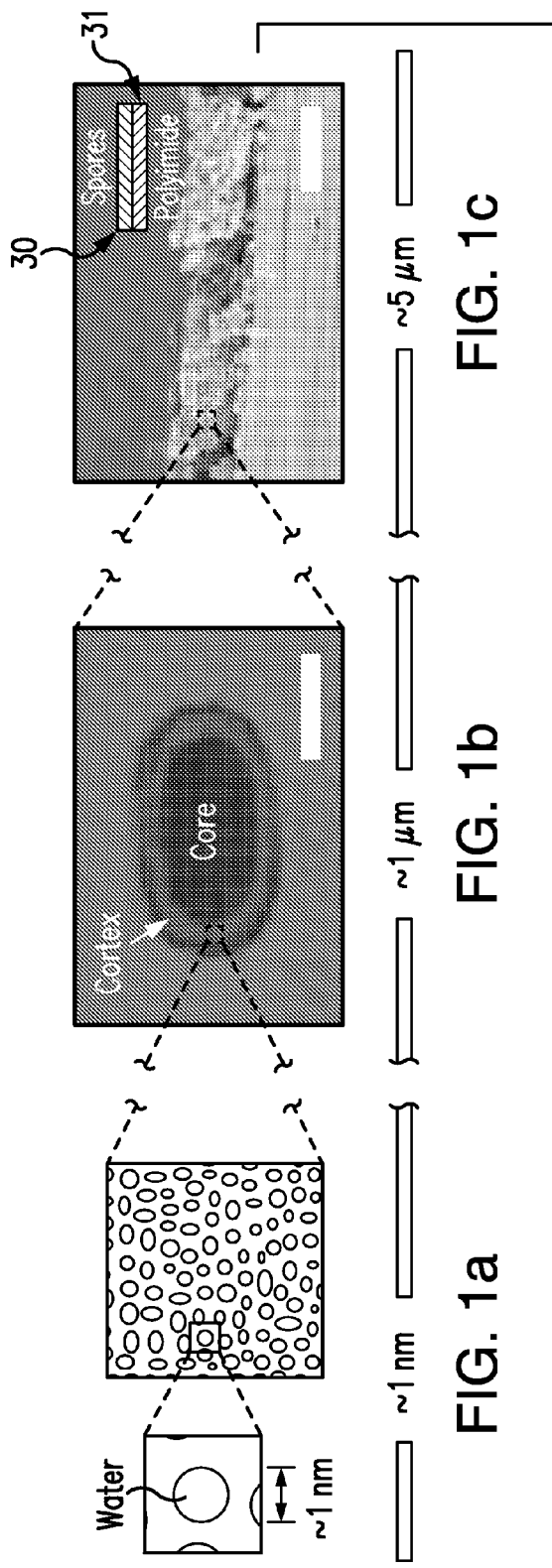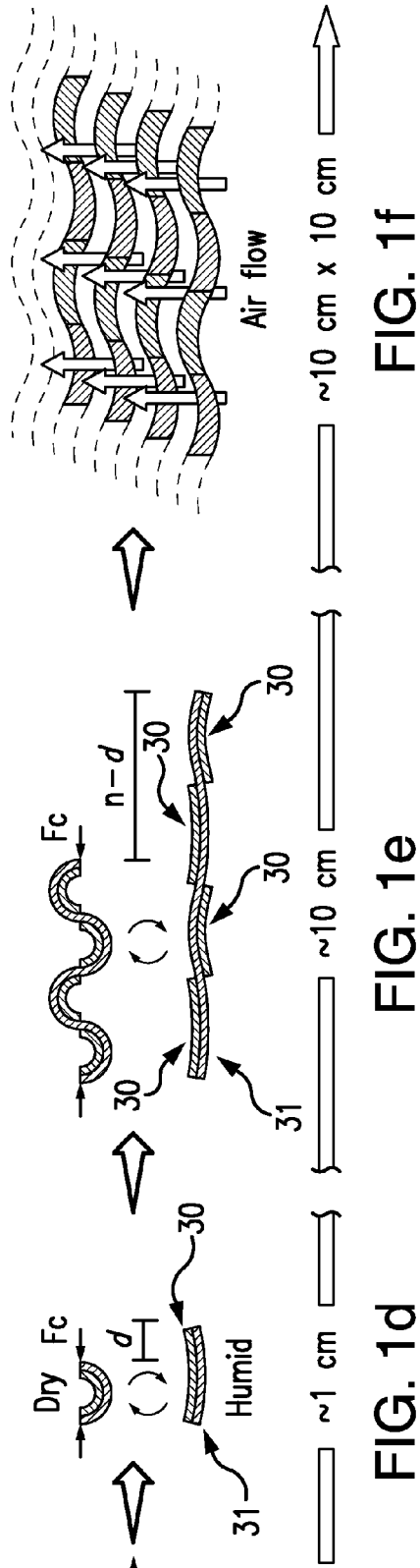

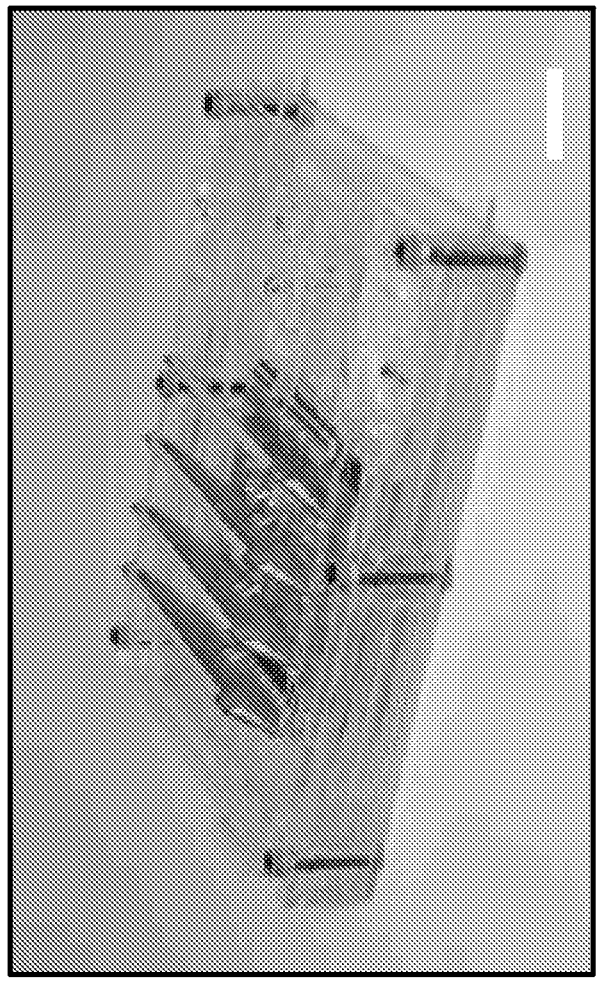
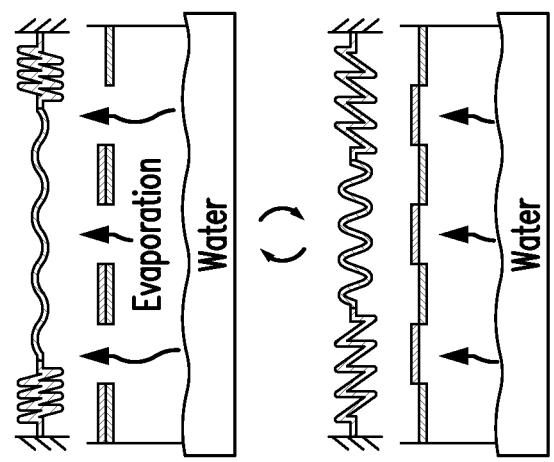
FIG. 2b
FIG. 2a

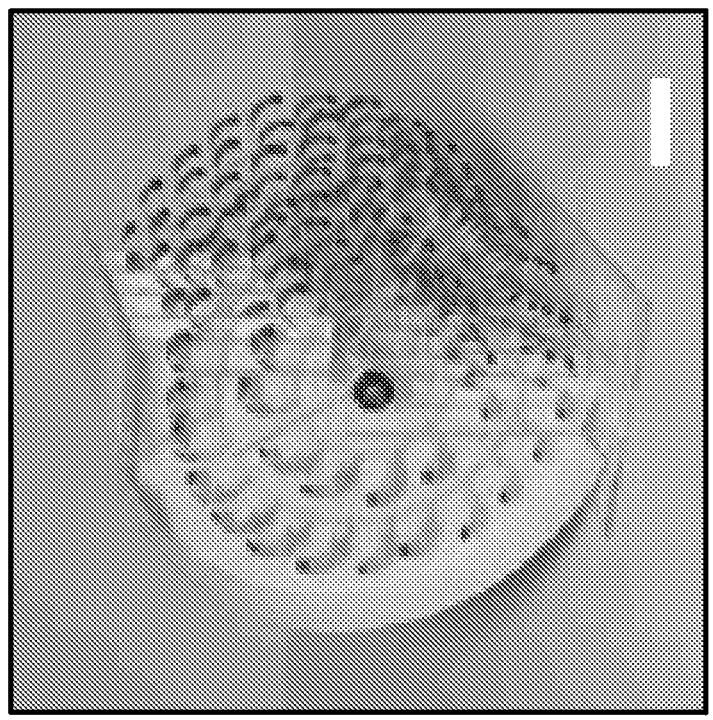
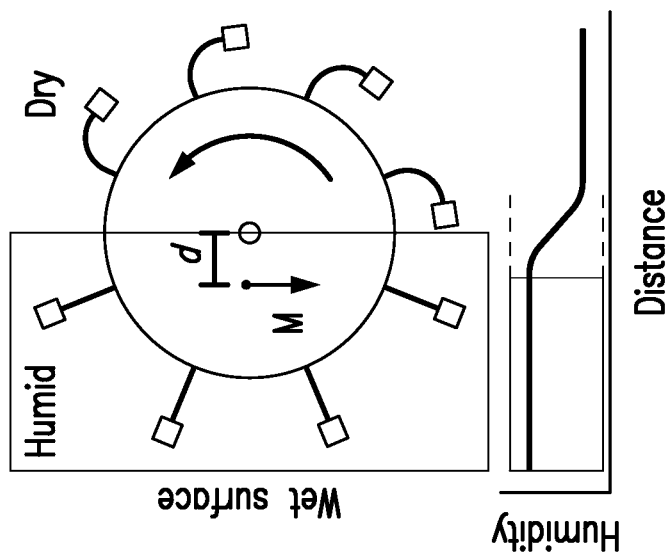
FIG. 3b
FIG. 3a

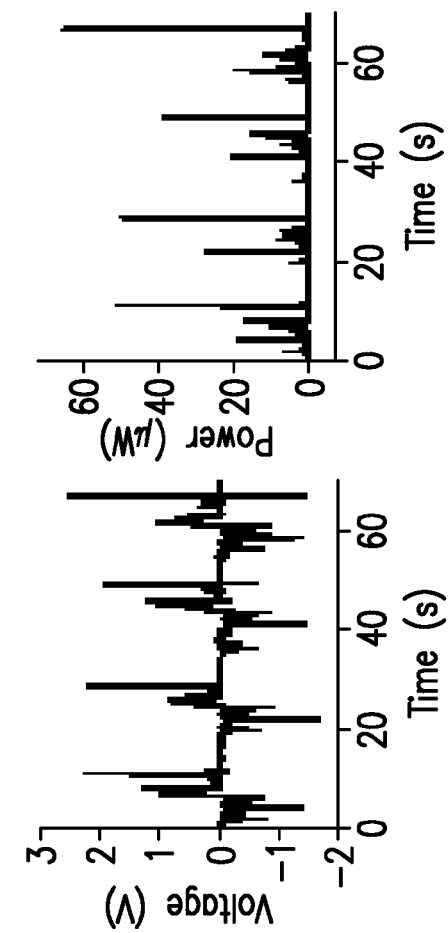
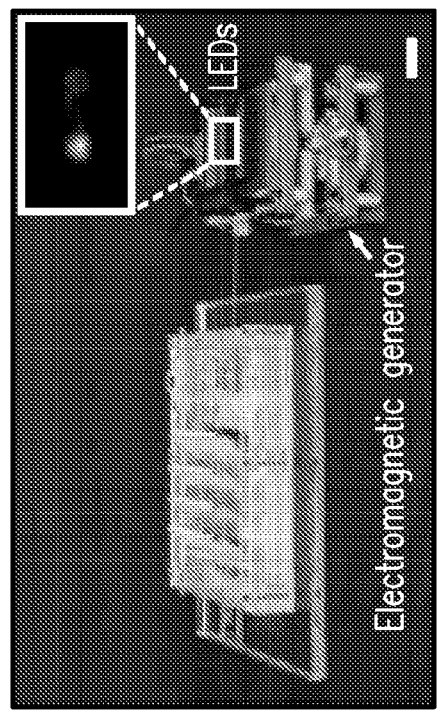
FIG. 8c
FIG. 8b
FIG. 8a

Polyimide tape

↓ Poly-L-lysine coating

↓ Poly-L-lysine coating

Spore/glue mixture coating

Spore/glue mixture coating

→ Drying

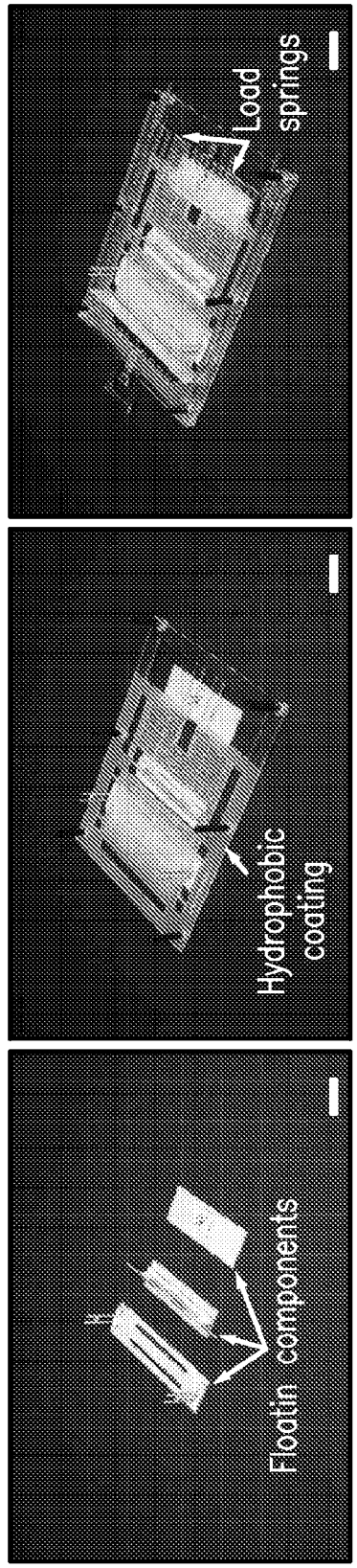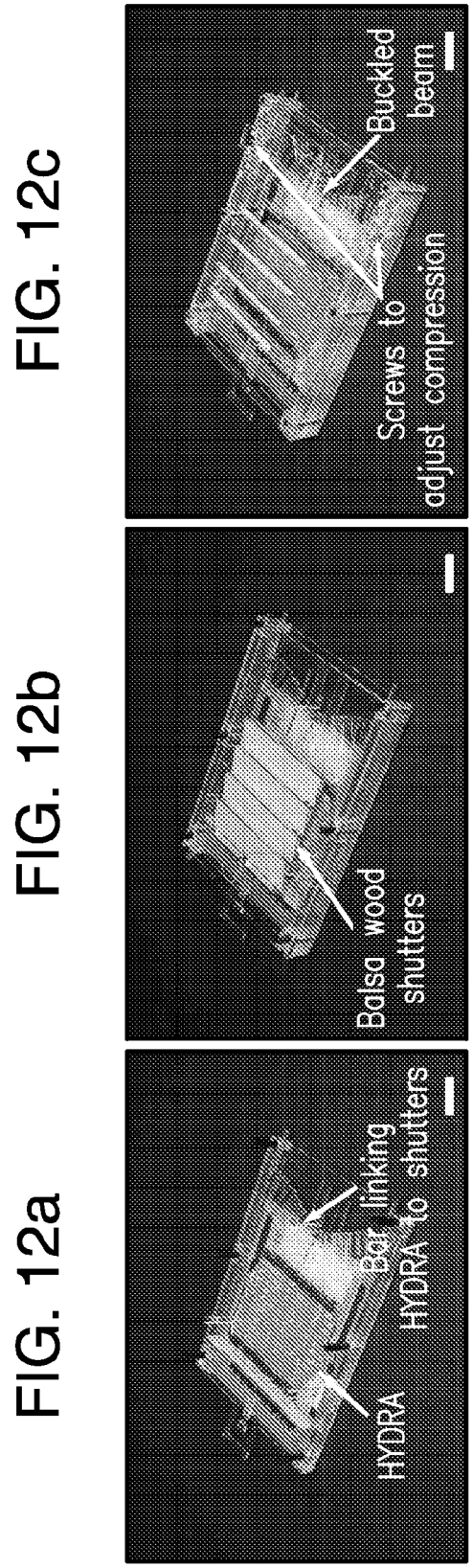

EVAPORATION-DRIVEN ENGINES

CROSS-REFERENCE TO RELATED APPLICATIONS

This application is a U.S. National Stage Patent Application under 35 U.S.C. § 371 of International Application No. PCT/US2015/029963, filed on May 8, 2015, which claims priority to U.S. Provisional Application Ser. No. 61/990,372 filed on May 8, 2014, the contents of each of which is are incorporated by reference herein in its their entirety.

STATEMENT REGARDING FEDERALLY SPONSORED RESEARCH

This invention was made with government support under Grant No. ER46847, awarded by the U.S. Department of Energy. The government has certain rights in the invention.

BACKGROUND

Evaporation is a natural phenomenon and a form of energy transfer in the Earth's climate. Nevertheless, evaporation as a source for powering engineered systems has not been fully explored. Nanoscale confinement of water in hygroscopic materials (i.e., objects that take up and retain moisture) can provide a way to convert energy from evaporation by generating mechanical force in response to changing relative humidity. However, scaling up this phenomenon to create macroscopic devices can face challenges: unfavorable scaling of hydration kinetics can slow down actuation speeds at large dimensions; small strains can complicate energy transfer to external systems; and the slow rate of change of relative humidity in the environment can limit the power output.

While evaporation carries a significant energy, it can involve a slow rate of water transfer that can limit the relative expansion and contraction of hygroscopic materials. Because the relative volume of the absorbed and released water can be small, the pressure change generated during this process should be large for efficient energy conversion. Water confined to nanoscale cavities within hygroscopic materials (FIG. 1a) can induce large pressures in response to changing relative humidity; however, these nanostructures can also limit the transport kinetics of water. Simply scaling up the dimensions of hygroscopic materials would not increase power, and can even lead to a decrease, because the time scale of wetting and drying can depend on the square of the travel distance of water.

Addressing the issues in transport kinetics alone would not necessarily be sufficient to increase power, because in certain environmental conditions relative humidity changes on daily and seasonal timescales, which can be too slow. However, spatial gradients in relative humidity established near evaporating surfaces can provide an opportunity.

SUMMARY

The presently disclosed subject matter provides methods and systems for evaporation-driven engines.

According to one aspect of the disclosed subject matter, evaporation-driven engines are provided. In an exemplary embodiment, an evaporation-driven engine includes a water source, a supporting structure, and a hygroscopic material. The evaporation-driven engine can include a mechanism for force transmission to a load. The water source can include a high humidity zone proximate the surface of the water source. The hygroscopic material can be disposed on the base and configured to generate mechanical force in response to a changing relative humidity. The hygroscopic material can be repeatedly exposed to the high humidity zone and removed from of the high humidity zone thereby causing the hygroscopic material to generate mechanical force. In some embodiments, a portion of the power generated by the hygroscopic material can be used to control the evaporation rate or move the hygroscopic material in and out of the high humidity zone, thereby causing the hygroscopic material to generate a mechanical force.

In some embodiments, the hygroscopic material can include bacterial spores. The spores can be *Bacillus subtilis* spores. In some embodiments, the base can be a sheet. The sheet can be a polyimide sheet or a rubber sheet. In some embodiments spores can be mixed with an adhesive to enhance interaction with the sheet and among spores. The adhesive can be polyvinyl acetate based glue.

In some embodiments, the hygroscopic material can be disposed on a first side of the sheet. In some embodiments, the hygroscopic material can be disposed alternately on a first side of the sheet and on a second side of the sheet. The evaporation-driven engine can include a plurality of support structures, each support structure having hygroscopic material disposed thereon.

In some embodiments, the hygroscopic material can be repeatedly exposed to the high humidity zone and removed from the high humidity zone by moving the hygroscopic material. The volume of the high humidity zone can change over time. The hydgroscopic material can be repeatedly exposed to the high humidity zone and removed from the high humidity zone by varying the high humidity zone. In some embodiments a shutter can be used to vary the high humidity zone. The shutter can be disposed between the surface of the water source and the hygroscopic material. The hygroscopic material can be disposed between the surface of the water source and the shutter. The water source can be a body of water.

In another exemplary embodiment of the disclosed subject matter, an evaporation-driven engine for creation of linear motion is provided. The evaporation-driven engine can include a water container, at least one hygroscopy driven artificial muscle (HYDRA). The water container can have a water pool and a shutter mechanism. The water pool can be a lake, reservoir, or other bodies of water. The shutter mechanism can be moveable between an open configuration, in which the water container is open and a closed configuration, in which the water container is closed. The HYDRA can be suspended above the water pool. Each HYDRA can have an extended position and a contracted position and each HYDRA can be configured to transition from the extended position to the contracted position in relatively low humidity and transition from the contracted position to the extended position in relatively high humidity. The mechanical load can be configured to hold the HYDRA in tension. The HYDRA can be functionally coupled to the shutter mechanism such that when the HYDRA transitions from the extended position to the contracted position, it causes the shutter mechanism to close, and when the HYDRA transitions from the contracted position to the extended position, it causes the shutter mechanism to open. The evaporation-driven engine can include a mechanical load.

Each HYDRA can include a supporting structure and a hygroscopic material disposed alternately on a first side of the supporting structure and on a second side of the supporting structure. The HYDRA can include a plurality of HYDRAs. The evaporation-driven engine can include a bistable element disposed between the at least one HYDRA and the shutter mechanism. The HYDRA can be functionally coupled to an electromagnetic generator. The evaporation-driven engine can include a protection layer disposed between the water and the HYDRA such that the HYDRA does not contact the water. The evaporation-driven engine can include a floating element configured to float on the water and support the HYDRA. A shutter can be disposed between the surface of the water source and the hygroscopic material. The hygroscopic material can be disposed between the surface of the water source and the shutter. In some embodiments, the water source can be a body of water.

In another exemplary embodiment of the disclosed subject matter, an evaporation-driven engine for creation of rotary motion is provided. The evaporation-driven engine can include at least one disk, an axle, a plurality of HYDRAs, and a humidity chamber. The disk can have a circumference region and a center. The axle can be disposed through the center of the disk such that the disk can rotate freely about the center. Each HYDRA can include a first end, a second end. Each HYDRA can include a weight disposed on the second end. Each first end can be coupled to the circumference region of the disk such that the HYDRAs extend and contract radially relative the disk. Each HYDRA can have an extended position and a contracted position, and each HYDRA can be configured to transition from the extended position to the contracted position in relatively low humidity and transition from the contracted position to the extended position in relatively high humidity. The humidity chamber can be configured to enclose a portion of the disks, such that a first subset of the HYDRAs are disposed within the humidity chamber and are in an extended position, and a second subset of the HYDRAS are disposed outside the humidity chamber and are in the contracted positions. The center of mass of the disk can be offset horizontally from the center of the disk due to the first subset of HYDRAs being in the extended position and the second subset of HYDRAs being in the contracted position, thereby causing a torque which can create rotational motion of the disk about the center and can cause the first subset of HYDRAs that are disposed within the humidity chamber to rotate out of the humidity chamber and transition from the extended position to the contracted position, and the second subset of HYDRAs that are disposed outside the humidity chamber rotate into the humidity chamber and transition from the contracted position to the extended position thereby sustaining rotational motion. The weights disposed on the second ends of HYDRAs can be varied to adjust torque and the rotation speed.

Each HYDRA can include a supporting structure and a hygroscopic material disposed on a first side of the sheet. The disk can include a plurality of disks. The humidity chamber can include a paper lining, and the paper lining can be wetted by water. In some embodiments, Each HYDRA can include a supporting structure and a hygroscopic material disposed alternately on a first side of the supporting structure and on a second side of the supporting structure. The HYDRAs can extend and contract radially outwardly from the disk. The HYRDAs can extend and contract radially inwardly from the disk.

In one embodiment, the rotational motion of the rotary engine can be coupled to wheels attached to a base. The rotary engine can be coupled to the wheels by a belt or by gears that transmit rotational motion.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter.

BRIEF DESCRIPTION OF THE FIGURES

FIGS. 1(a)-(f) illustrate an example procedure for scaling up hydration-driven nanoscale energy conversion in accordance with the disclosed subject matter.

FIG. 2 illustrates (a) schematics and (b) an image of an evaporation-driven engine for creation of linear motion in accordance with the disclosed subject matter.

FIG. 3 illustrates (a) a schematic and (b) an image of an evaporation-driven engine for creation of rotary motion in accordance with the disclosed subject matter.

FIG. 8 illustrates (a) an evaporation-driven engine used to light LEDs, and (b)-(c) related experimental results.

FIGS. 12 (a)-(f) illustrate parts of an evaporation-driven engine for creation of linear motion in accordance with the disclosed subject matter.

DETAILED DESCRIPTION

The disclosed subject matter can be used for making and using evaporation-driven engines. The evaporation-driven engines can use hygroscopic materials, for example, bacterial spores, to generate power, and at least a portion of the power generated by the hygroscopic materials can be used to control the evaporation rate of water, or move the hygroscopic materials in and out of the high humidity zone at the surface. As such, the relative humidity experienced by the hygroscopic materials can change rapidly in a cyclical fashion. The evaporation-driven engines disclosed herein can start and run autonomously when placed at air-water interfaces, and can operate as long as the air is not saturated. The disclosed subject matter can be used for industrial applications or for toys, for example, to power toy cars or boats.

Figure 5C:
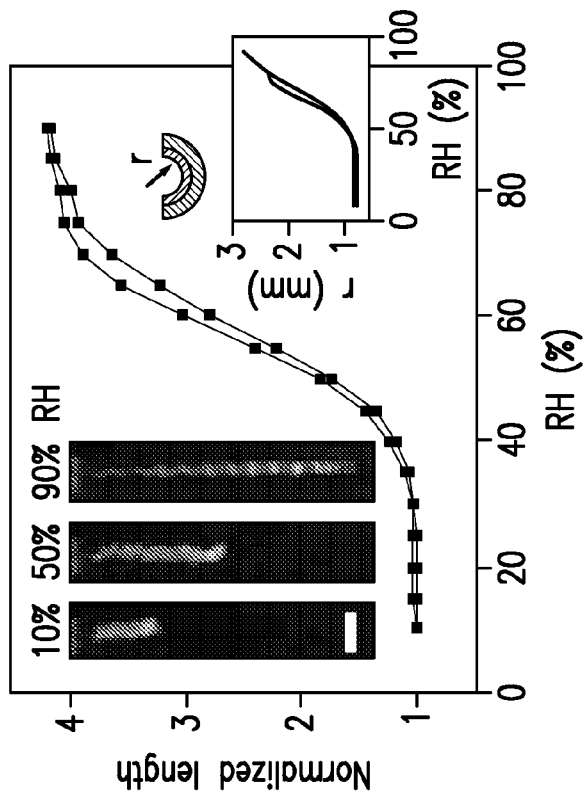
FIG. 5 illustrates (a)-(b) hygroscopy-driven artificial muscles in accordance with the disclosed subject matter, and (c)-(e) related experimental results.
Figure 5B:
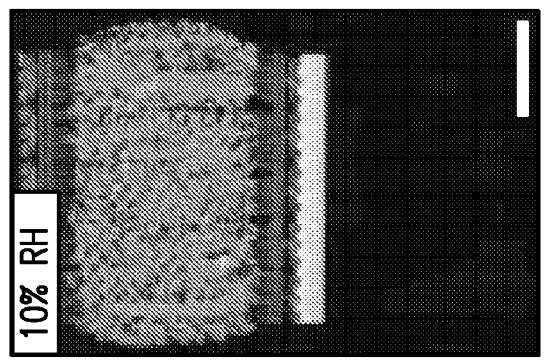
Figure 5A:
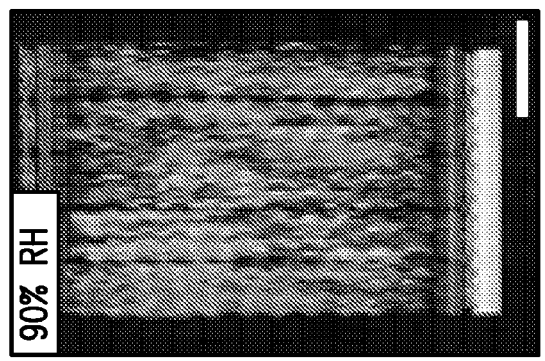
Figure 5E:
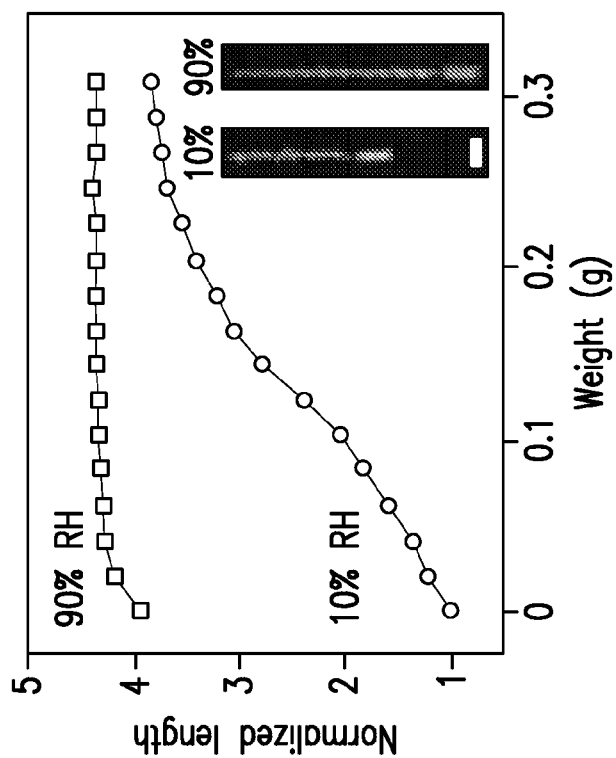
Figure 5D:
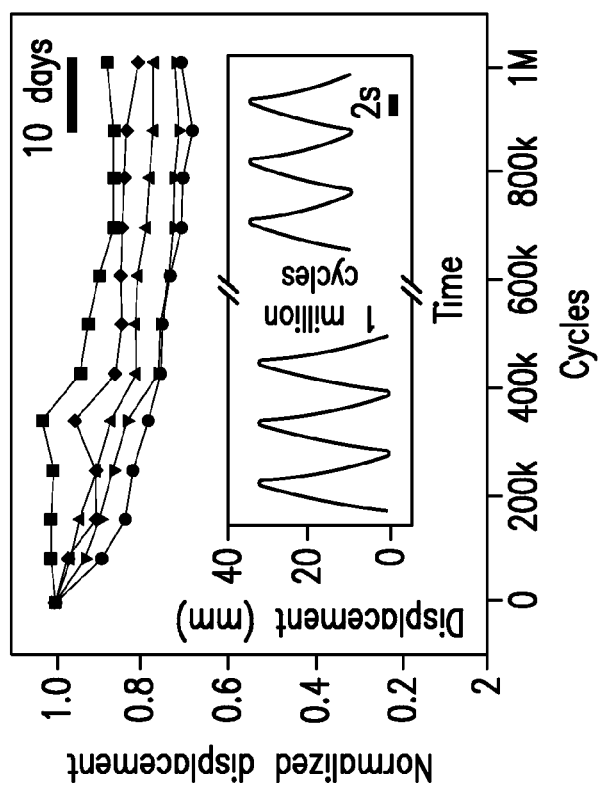
Figure 6C:
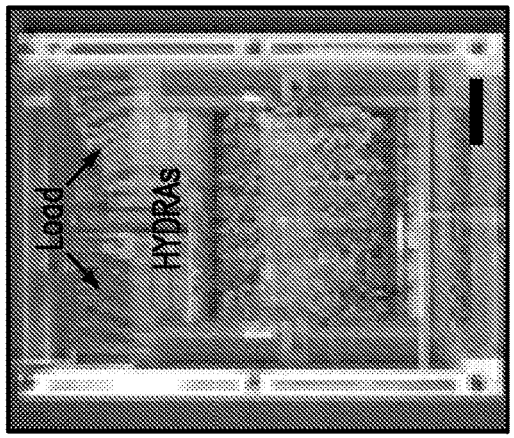
FIG. 6 illustrates (a)-(c) schematics of an evaporation-driven engine for creation of linear motion in accordance with the disclosed subject matter, and (d) related experimental results.
Figure 6D:
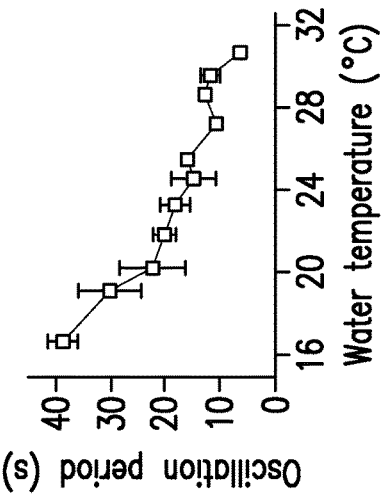

A hierarchal design strategy can be used to enhance water transport kinetics in evaporation-driven macroscopic systems. As noted above, water confined to nanoscale cavities within hygroscopic materials (FIG. 1a) can induce large pressures in response to changing relative humidity. Bacterial spores (30) can be deposited on micrometer thick plastic films (31) (FIG. 1b,c). These films can change curvature as a function of relative humidity (FIG. 1d). The overall movement can be made linear by coating alternating sides of longer tapes with spores (FIG. 1e), which can enable a linear displacement at both ends of the hygroscopic material in response to a humidity change. The linear displacement can allow stacking multiple sheets together. Stacked sheets can form a planar actuator having a motion is primarily in the plane defined by the actuators (FIG. 5a). The in plane motion facilitates placement of the stacked sheets parallel to the surface of water which is also planar, as described in greater detail below. The sheets expand and contract horizontally, without moving away from the water surface, which can decrease leakage of moisture into the air without being absorbed by the hygroscopic material. An example preparation process of longer tapes is shown in FIG. 11. Assembling several tapes as a stack, while leaving air gaps between each layer can facilitate moisture transport to and from the spores, and can result in a material that can be scaled in two dimensions without compromising hydration/dehydration kinetics (FIG. 1*f*). The layered architecture can increase the surface area for evaporation and condensation and the small thickness of the spore layer (for example about 3 μm) can reduce the travel distance of the water within the nanostructured material. Scaling up the size of the material in two dimensions can proportionally increase the surface area for evaporation and condensation, while keeping the thickness of the spore layer constant. Note that the particular wavy design in FIG. 1*f* also has the advantage of enhancing the effective actuation strain.

Two exemplary embodiments are presented to expose hierarchically designed hygroscopic materials to rapidly changing relative humidity. Each embodiment is presented in greater detail below. In a first embodiment, a shutter mechanism is used to control evaporation rate (FIG. 2*a*). Coupling the expansion and contraction of the spore-coated films to the shutters can result in a self-starting oscillatory movement with net power output. FIG. 2*b* shows an example device that can exhibit oscillations when placed above water. In some embodiments the shutter mechanism can be disposed between the water surface and the spore-coated film (FIG. 2*a*) and in some embodiments, the spore-coated film can be disposed between the water surface and the shutter mechanism (FIG. 6*a*). When the shutters are closed, moisture evaporating from the water surface can fill the region below the shutters and can extend the high humidity zone. When shutters are open, moisture can leak out and the high humidity zone can be confined to the immediate vicinity of the water surface, leaving the spore-coated films outside the high humidity zone and in a lower humidity condition. In a second embodiment, spores are moved in and out of the humid zone. This can be achieved by coupling hydration-induced movement to a rotational motion. For example, gradients in relative humidity near the evaporating surface can induce different degrees of curvature in spore-coated films assembled around a freely rotating disk (FIG. 3*a*). The horizontal shift in the center of mass of the entire structure can create torque that can sustain rotational motion. FIG. 2*b* shows an exemplary embodiment that exhibits continuous rotation when the paper lining the inner surface of the device, is wetted.

FIGS. 4*a* and 4*b* show, for the purpose of illustration and not limitation, an 8 μm-thick polyimide tape coated with an approximately 3 μm-thick spore layer (using *Bacillus subtilis* spores missing most of their outer protein protective layers, due to mutations in cotE and gerE) changing its curvature in humid and dry conditions. Using the design outlined in FIGS. 1*c-f*, longer tapes can be created and assembled in parallel. FIGS. 4*c* and 4*d* show, for the purpose of illustration and not limitation, the resulting changes in overall length of the tapes in humid and dry conditions. When assembled in parallel, these tapes can lift weight against gravity in dry conditions (FIG. 5*a,b*). Due to their hygroscopy driven responses, these actuators are referred to herein as hygroscopy driven artificial muscles (HYDRAs).

The actuation behavior of individual HYDRA strips can be characterized by placing the strips inside transparent plastic tubes and flowing air with changing relative humidity. FIG. 5*c* shows, for the purpose of illustration and not limitation, that HYDRAs can quadruple in length as the relative humidity changes from below 30% to above 80%, with little hysteresis in the response curve. The amount of moisture absorbed by the HYDRAs in this process is less than 5% by weight (measured from the differences in strip weights at low and high relative humidity). The average curvature of individual arcs, estimated from the overall lengths of strips, vary from 0.7 mm to 2.8 mm. The response curve in FIG. 5*c* exhibits an “S” like shape. The response is saturated at high RH, because as the radius of curvature of each arc increases, the end-to-end distances of arcs can converge to the contour length of the strip. At the lower RH region, spores approach their fully dehydrated size and this effect can limit the degree of contraction observed in the HYDRA strip.

Test of the stability of actuation performance can show that the extension of strips reduces only slightly even after 1 million cycles and 80 days (FIG. 5*d*). The strips can show a similar degree of performance reduction when they are subjected to a load weight of 0.1 g. The time dependent displacement data shown in FIG. 5*d*, for the purpose of illustration and not limitation, shows that the HYDRA strips can respond to changes in relative humidity within approximately 3 seconds. This can be sufficiently fast for practical applications.

When loaded with increasing weight, the range of motion can reduce, but can remain significantly even at load weights that are 50 times more than the strips (0.31 g v. ~6 mg). Using the force-distance measurements (FIG. 5*e*), the work density of the entire strip can be estimated (by dividing the area enclosed by the curves in FIG. 5*e* to the weight of the strip), to be approximately 17 J $kg^{-1}$, which is close to mammalian skeletal muscles, but comes with extremely large strain. Taken together, HYDRAs can require little moisture for activation and can generate strains and work densities that can facilitate development of evaporation driven engines. These characteristics can permit HYDRA applications beyond evaporation driven engines, as artificial muscles and bio-hybrid cell-based actuators for soft robotic systems.

Using HYDRAs, oscillatory devices that allow and block evaporation in a cyclical fashion can be developed, so that energy can be continuously extracted from evaporation. While hygroscopic materials can exhibit spontaneous oscillatory motion due to turbulence or geometric nonlinearities, these movements can be difficult to control and use in devices. To induce oscillations deliberately, oscillator designs commonly used in electrical circuits can be used. For example, a relaxation oscillator that relies on a bistable circuit element (e.g., a Schmitt trigger) that is held under feedback control. The relaxation oscillator circuit can repeatedly switch between two internal states. The basic architecture of a hygro-mechanical oscillator, in accordance with the disclosed subject matter, can be designed in analogy with this relaxation oscillator. FIGS. 6 and 7 shows, for the purpose of illustration and not limitation, how example HYDRAS coupled to a buckling beam and a shutter mechanism form a relaxation oscillator.

Figure 6A:
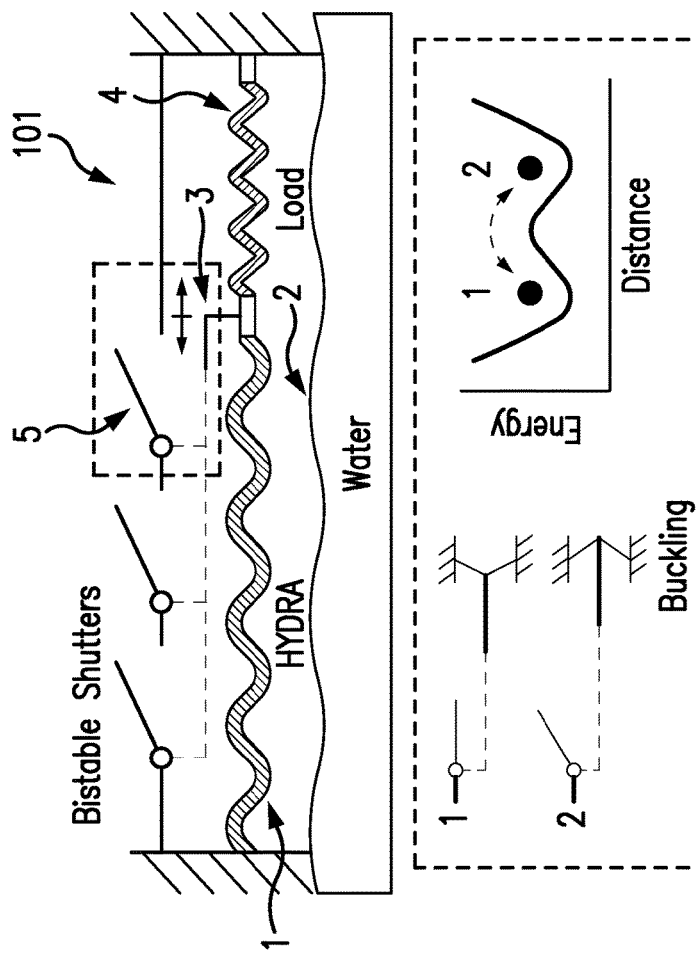
Figure 6B:
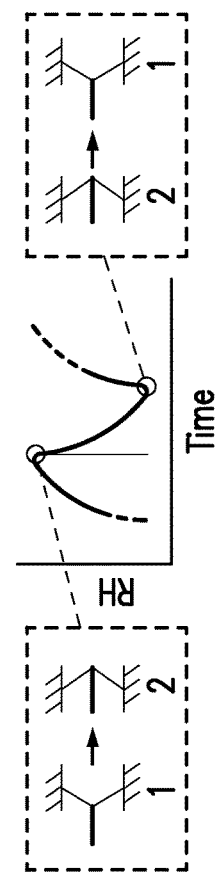
Figure 7:
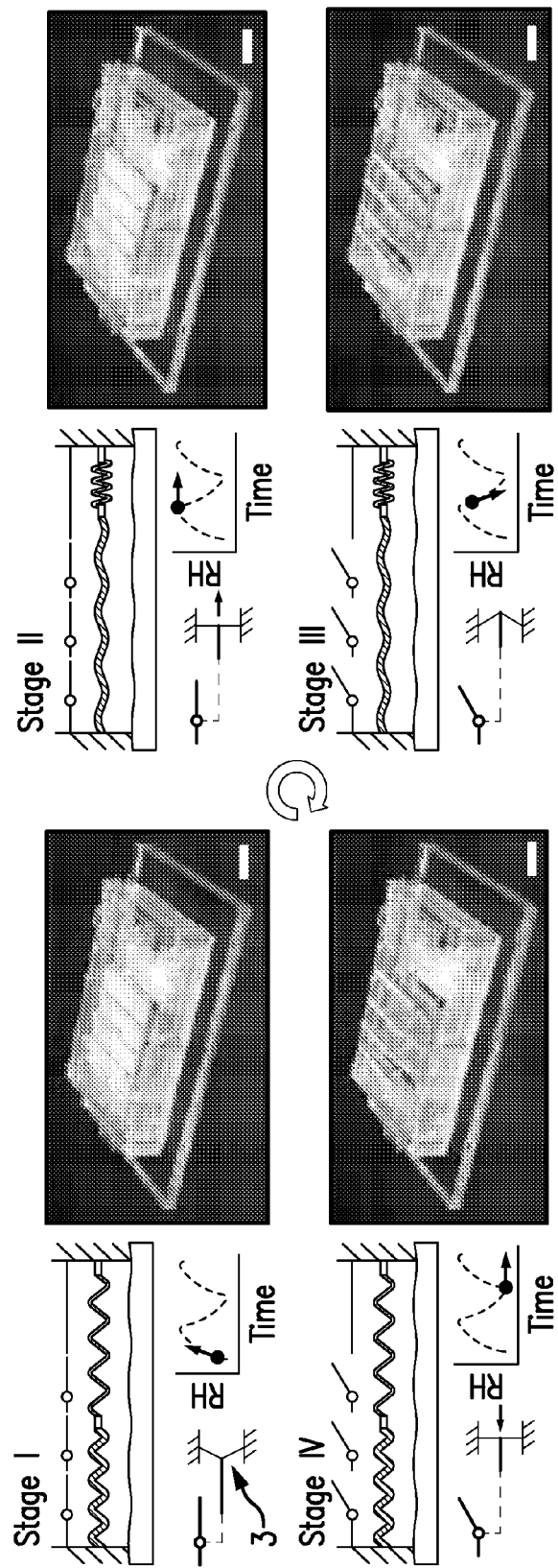
FIG. 7 illustrates the four stages of oscillatory motion of an evaporation-driven engine for creation of linear motion in accordance with the disclosed subject matter.

With reference to FIG. 6a, for the purpose of illustration and not limitation, a evaporation-driven engine for creation of linear motion 101, includes HYDRAs 1 placed horizontally above the water surface 2 and coupled to a bistable element 3 (e.g., a buckle beam). A load spring 4 can hold the HYDRAs under tension. The HYDRAs and the bistable structure can be supported by floating components, for example, as shown in FIG. 12a). These floating components can rest on the surface of water and can be free to move horizontally to reduce the tension caused by the weights of HYDRAs, and thus increase the force provided by HYDRAs for external work. The buckled beam can control a shutter mechanism 5 that can allow or block passage of moist air, which can provide feedback (FIG. 6b). The engine 101 can exhibit oscillations with four stages (FIG. 7).

In some embodiments, the water can be a body of water, for example, a lake, pond, reservoir, pool or other body of water. The evaporation-driven engine can float on the body of water, such that the water container 6 is open on the bottom to allow water from the body of water to enter the water container. Thus, the water surface 2 can be provided by the body of water. Such a configuration can utilize water that evaporates naturally, and thus does not consume water.

FIG. 6d shows, for the purpose of illustration and not limitation, the average period of oscillations as a function of water surface temperature (controlled by a heater placed below the water container). The temperature and relative humidity, and flow rate of the surrounding air was maintained at 25° C., 20%, and 0.6 m/sec, respectively. The data shows that the increasing of water surface temperature shortened the period of oscillation (FIG. 6d). The device exhibited oscillations even with a water surface temperature well below the air temperature (16° C. v. 25° C.). The most rapid oscillations, observed at 31° C., had a period of about 6 seconds. (Measurements beyond this temperature were not taken to prevent condensation). This trend in FIG. 6d can be explained by the temperature dependence of the vapor pressure at the water surface, which affects the evaporation rate significantly. The period of oscillations observed with this oscillator shows that despite the slow natural variations in relative humidity, it is possible to create rapid motions by actively modulating evaporation rates at surfaces.

The rapid piston-like motion of the oscillator allows it to act as an engine, supplying power to external systems. For example, the oscillatory engine can be connected to a generator (FIG. 8) and can supply electricity to light emitting diodes (LEDs). Water temperature can be maintained at 30° C. Depending on the direction of the oscillatory motion, two oppositely connected LEDs gave light repeatedly and in alternating order. The LED was replaced with a resistor and the electrical power was measured (FIG. 8 b,c). The time course of the voltage across the 100 kΩ resistor and the corresponding power showed that energy was supplied in bursts at power levels reaching 60 µW. Waiting periods that separate these bursts bring the average power to 1.8 µW. These waiting periods could potentially be reduced with more compact designs so that humidity levels change more rapidly. Nevertheless, the ability to generate light with LEDs and the microwatt scale power measured with a load resistor is still significant, especially when the small area of water covered by the HYDRAs (9.6 cm by 7.6 cm) is considered.

Figures 9A, 9B:
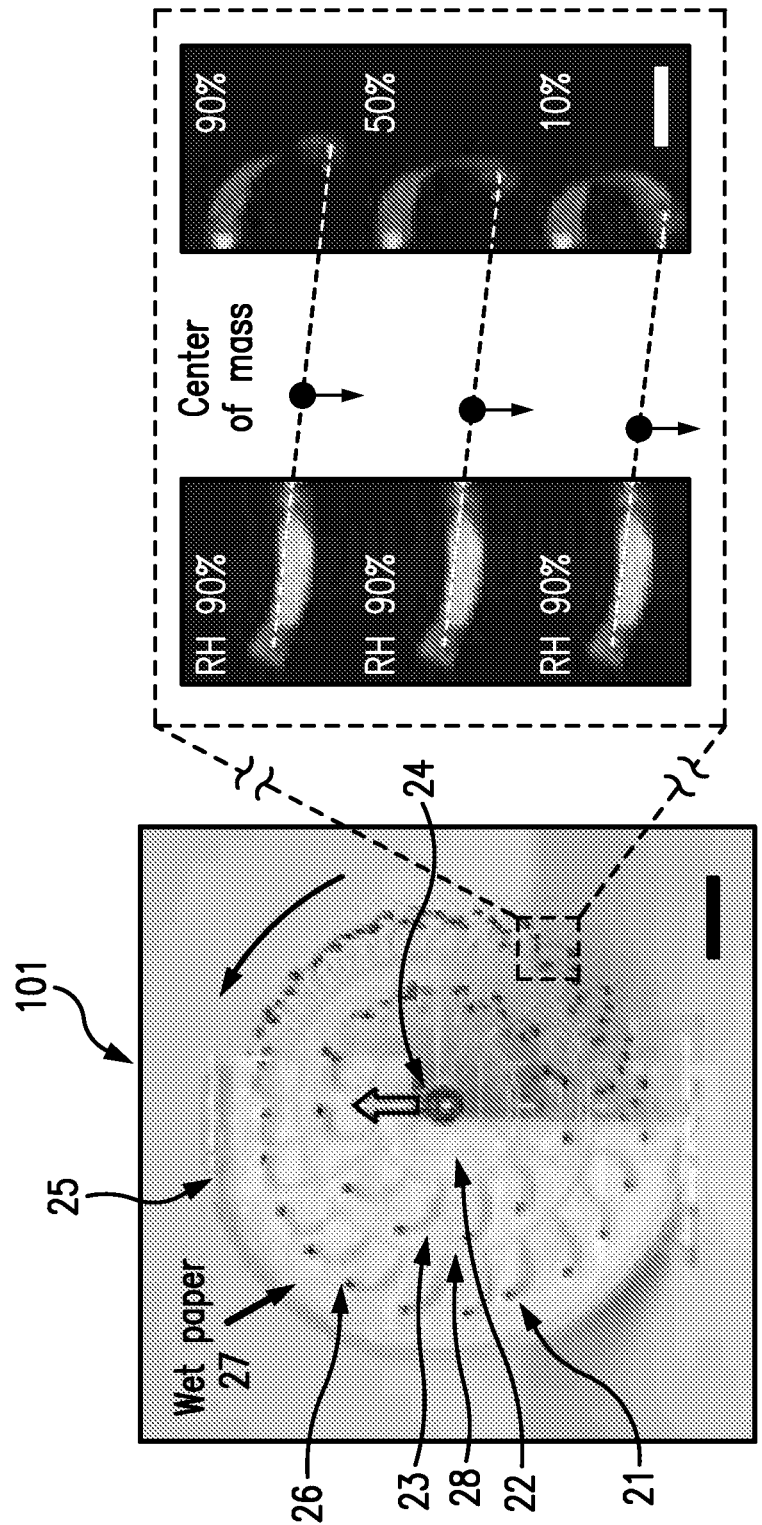
FIG. 9 illustrates (a)-(b) an evaporation-driven engine for creation of rotary motion in accordance with the disclosed subject matter, and (c)-(d) related experimental results.

Many devices, particularly those that are used for locomotion, utilize rotary motion. Using the design concept illustrated in FIG. 3a, and with reference to FIG. 9a, for the purpose of illustration and not limitation, an evaporation-driven engine for creation of rotary motion 102 (moisture mill) is provided. The engine 102 includes HYDRAs 21 assembled around two concentric rings (also referred to herein as disks) 22, 23. The HYDRAs 21 can be coupled to a circumference region 28 of the rings. The concentric rings 22, 23 can be laser-cut from acrylic glass. Four or five such structures can be connected in parallel via a central axis 24. The entire structure can rotate freely around ball bearings. As shown in FIGS. 3a and 9a, the structure can be inserted halfway into an enclosure 25 such that the HYDRAs face walls lined with paper 27 (the outermost wall is removed to allow the HYDRAs to be viewed). To increase torque, small blocks 26, for example made of acrylic, can be attached at the HYDRAs free ends. In some embodiments, weights coupled to the free ends of the Hydras can be connected to one another. In some embodiments, an outer ring can be coupled to the free end of the HYDRAs. Figures (FIG. 9b) and measurements (FIG. 9c) illustrate, for the purpose of illustration and not limitation, that the horizontal displacement of the acrylic block was as much as 5.5 mm when the relative humidity on the right side was reduced relative to the left side. As a result of this, the structure began to rotate when the paper was wetted. Measurements (FIG. 9d) show that the rotational speed can depend on the relative humidity outside the chamber and the speed of airflow near the device. The increase in rotational speed with flow rate can be explained by the more efficient mixing with the surrounding air. Airflow specifically directed at HYDRAs can induce torque to rotate the structure. The effect can be negligible, since the data show that beyond a certain relative humidity, the rotations stop despite the presence of airflow.

Figure 10:
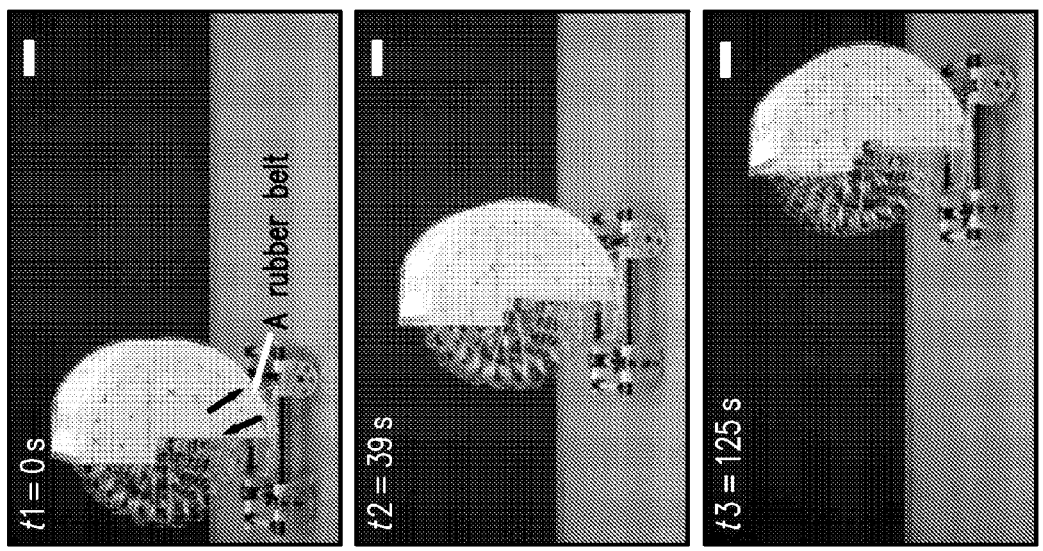
FIG. 10 illustrates a car driven by an evaporation-driven engine.
Figure 11A:
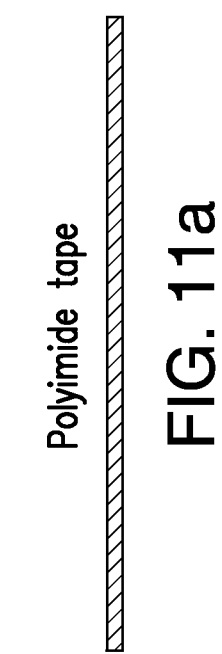
FIGS. 11 (a)-(f) illustrate an example assembly process for long hygroscopy-driven artificial muscles in accordance with the disclosed subject matter.
Figure 11B:
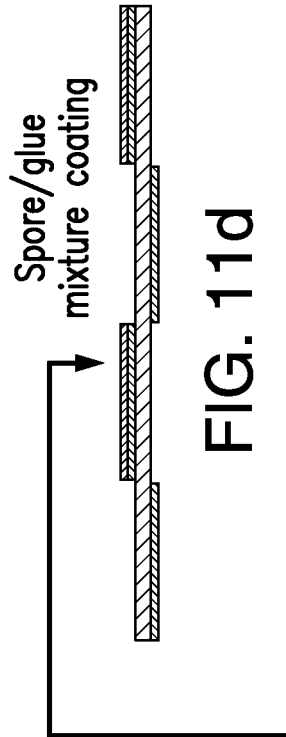
Figure 11C:
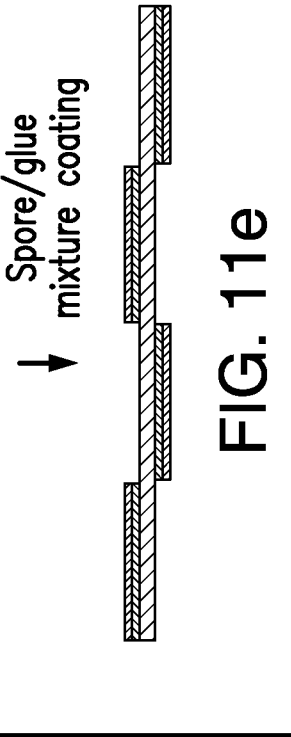
Figure 11D:
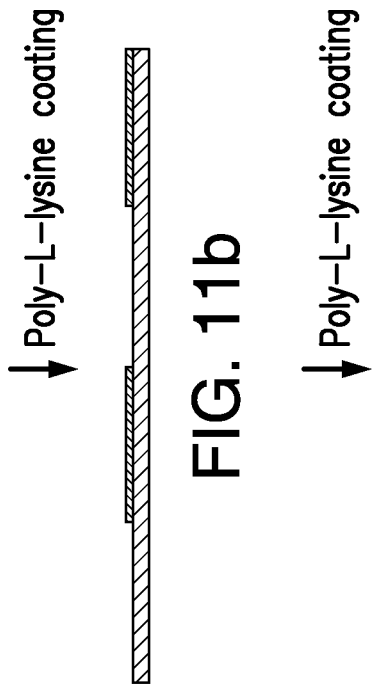
Figure 11E:
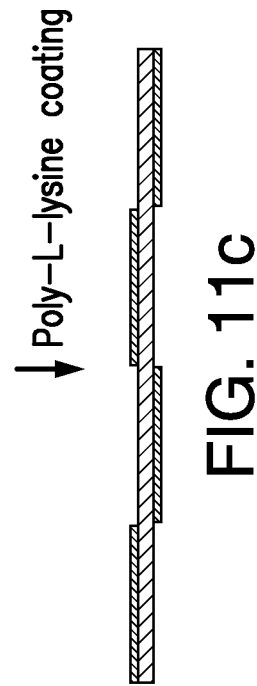
Figure 11F:
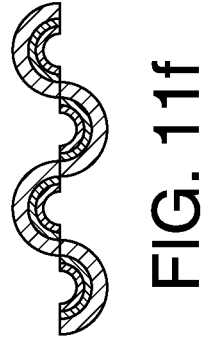
Figure 13E:
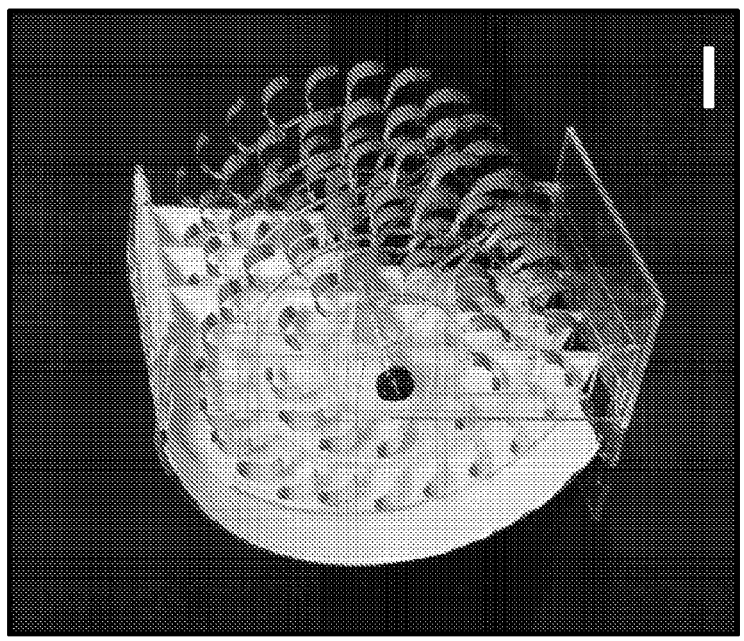
FIGS. 13 (a)-(e) illustrate parts of an evaporation-driven engine for creation of rotary motion in accordance with the disclosed subject matter.
Figure 13B:
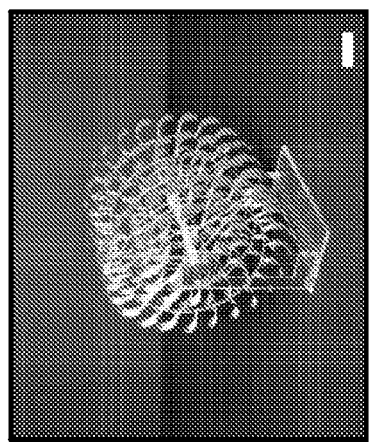
Figure 13D:
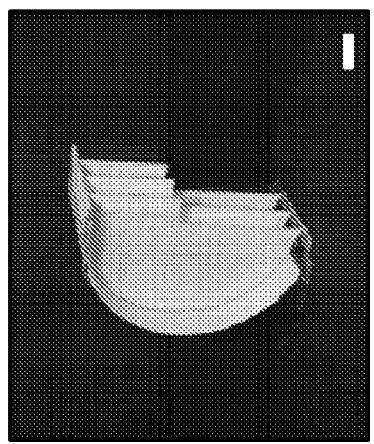
Figure 13A:
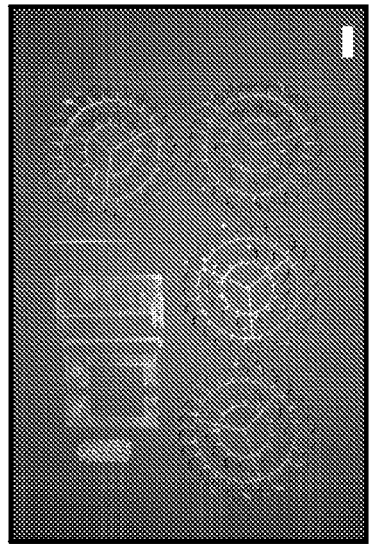
Figure 13C:
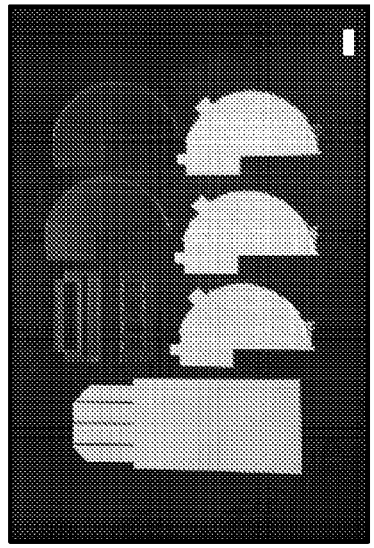

A miniature car can be created by placing the engine 102 above a frame attached to two pairs of wheels, and coupling the engine's rotation to the front wheels with a rubber belt. As the water in the wet paper evaporates, the engine pushes the 0.1 kg car forward (FIG. 10).

The disclosed subject matter provides strategies to scale up a nanoscale energy conversion mechanism to create macroscopic devices. Many interesting nanoscale phenomena can benefit from increased surface to volume ratios at small length scales. However, this property can also come with a price due to slow kinetics that begin to dominate as one tries to scale up the sizes of the structures. The disclosed subject matter shows that this challenge can be mitigated in the case of hydration driven systems and can also be applicable to other systems driven by chemical stimuli. In addition, from a technological standpoint, the disclosed subject matter, e.g., the evaporation driven car and the powering of LEDs highlight the so-far overlooked capability of water in the environment to supply useful levels of power. Due to the ubiquity of evaporation in nature and the low cost of materials involved (plastic tapes, hygroscopic materials), the engines presented here can find applications as energy sources for a wide range of off-the-grid systems that function in the environment.

Figure 4A:
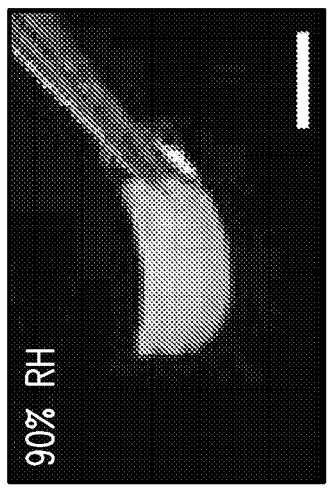
FIGS. 4 (a)-(d) illustrate spore-coated polyimide tapes at low and high relative humidity.
Figure 4B:
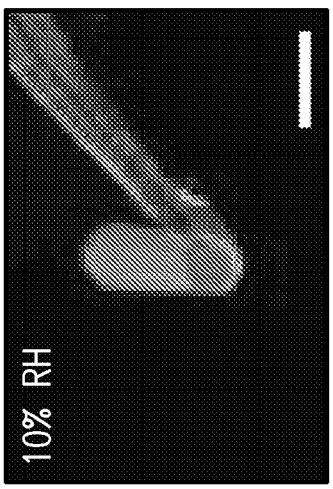

The preparation process of small HYDRA samples (FIG. 4a,b) can start by cutting 8 µm thick polyimide sheets (SPEX) into square pieces (4 mm×4 mm). 0.8 µL Poly-L-lysine solution (0.1 w/v ratio, Sigma-Aldrich) can be applied to the top surfaces of the samples using a micropipette and can be allowed to dry in an environment at a RH of ~40%. A spore suspension (cotE gerE mutant of *Bacillus subtilis*) can be mixed with a solution of multi-purpose glue (Elmer's Products) (~2.4×10$^9$ spores for each 1 µl of glue) using a vortex mixer. The mixture containing approximately 4.8×

$10^8$ spores can be applied to the top surfaces of the Poly-L-lysine treated polyimide sheets using a micropipette and can be allowed to dry in RH of ~40%. Because the spores can be assembled on polyimide substrates at their fully hydrated state, the samples can present curvature once the mixture applied on the top surface dried out. The amount of spores can form an approximately 3 μm thick spore layer on top of polyimide substrates as judged by weight of the spore layer (the density of the spores can be assumed to be 1.5 g/cm$^3$).

Figure 4C:
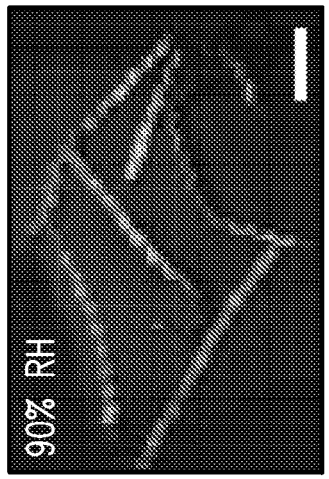
Figure 4D:
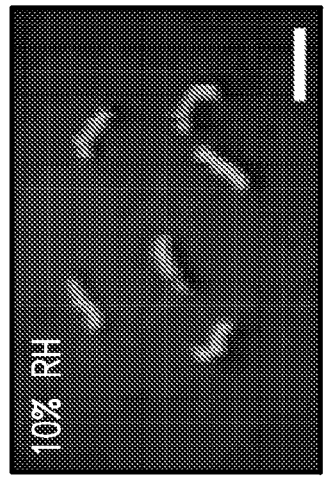

The preparation process of longer HYDRAs with wavy shapes (FIG. 4c,d) can include deposition of poly-L-lysing on alternating sides of 4 mm×96 mm polyimide tapes leaving equal spaces between each deposited region. The spore-glue mixture can be applied on the areas coated with poly-L-lysine, first on one side. The mixture can be allowed to dry in humid condition (~90% RH) to prevent curvature of individual regions before these longer HYDRAs are fully prepared. Then the tape can be flipped over and the same amount of the mixture can be deposited on the other side, giving the tapes their wavy shape.

To characterize HYDRA strips, individual HYDRAs can be attached to a piece of acrylic glass and then vertically placed in a transparent glass tube (McMaster-Carr). The RH can be monitored by placing a humidity sensor (HIH-4021, Honeywell) near the HYDRAs and can be recorded to a computer. A stream of air can be passed through the glass tube to vary the RH. Control of the RH can be achieved by mixing dry air (~5% RH) provided by a laboratory air source with humid air (~90% RH) generated by passing the laboratory air through a bubbler (An airstone from JW Pet Company can be used to bubble air into water in an Erlenmeyer flask). By controlling the flow rates of dry and humid air sources, the RH inside the glass tube can be varied from ~10% to ~90%. The lengths of the HYDRA strips can be measured with a digital camera. Curvatures of individual arcs (inset FIG. 5c) can be estimated by assuming that each arc has the same shape.

The amount of water absorbed by HYDRA strips can be measured from the changes in the total weight of 50 HYDRA strips at 10% and 90% RH. Independent of the HYDRA samples, the scale can give different readings at high RH and low RH, presumably due to increased air pressure at high RH. This component can be separately measured and subtracted from the measurements of HYDRA strips.

The stability of actuation performance of HYDRAs can be measured by alternating RH in the glass tube at a frequency of 0.15 Hz. A solenoid valve (SMC) and a power MOSFET (NTD4960N) can be used to switch the air from dry to humid by supplying a square wave using a function generator (Siglent SDG1020). Photos can be taken by a digital camera to monitor the extension of the HYDRA.

To estimate the forces generated by HYDRAs, the motion of HYDRAs with varying load attached can be tested when RH is alternated between ~10% and ~90%. Masses, made of acrylic glasses, can be increased during each trial from 0 g to 0.3 g in increments of 0.02 g. The work density can be estimated from the area enclosed by the displacement curves in dry and humid conditions.

The oscillatory engine can be made of stacked layers of laser-cut, 2 mm thick, acrylic glasses (McMaster-Carr, TAP Plastics). The layers can be held together by plastic bars going through the layers (plastic LEGO® rods). The bottom components can be floating structures that rest on the surface of water and are free to move horizontally. These floating layers can provide support for HYDRAs and the bistable structure above. These structures can be made of 1 mm thick Depron sheets (RCFOAM) and 0.8 mm thick Balsa wood (Dick Blick Art Materials) cut with a laser cutting system (Epilog Helix Laser). The protection layer, which can be coated by hydrophobic material (Hydrobead), can allow water vapor to permeate up and meanwhile protect HYDRAs from wetting. Above the protection layer is the frame (another acrylic layer) that can both provide physical support for HYDRAs and connect them to internal or external load. 84 HYDRA filaments, which cover a surface area of ~73 cm$^2$ (96 mm in length×76 mm in width), can be assembled on the support layer. A Balsa bar can be attached to the mobile end of HYDRAs to communicate with top layer controlling the shutter positions. The shutters can be fabricated by gluing (Elmer's Products) laser-cut Balsa wood and acrylic pieces together. The acrylic pieces on one end of Balsa wood surfaces can be used to balance the weight of the shutters. After attaching four individual shutter pieces on an acrylic substrate using 13 μm polyimide tapes (CAPLINQ) that can serve as flexible joints, the shutter layer can be placed on top of HYDRAs with a gap of ~8 mm. The oscillatory engine can be finished by assembling the final acrylic layer that can include of a bistable beam structure that can be adjusted using two screws placed at both ends of this structure. This final layer can advance and retract as the bistable beam switches its position. The shutters can be coupled to this layer with threads pulling in opposite directions. FIG. 12 shows various layers forming the device.

Individual HYDRAs for rotary engines can be prepared from 25 μm thick polyimide tapes (CAPLINQ) that can be cut into 6 mm×14 mm pieces. To increase the torque, blocks of acrylic with a weight of approximately 0.015 g can be attached to each HYDRA using multipurpose glue (Elmer's Products). The HYDRAs can be assembled, for example by glue, on acrylic rings, which can be cut from 1.5 mm thick acrylic glasses (McMaster-Carr). Individual disks can be placed on a stainless steel shaft (1.98 mm in diameter, McMaster-Carr) along with 2 mm thick acrylic spacers. The shaft can be supported by two ball bearings (VXB) that can be assembled on an acrylic base. The humid enclosure can include cellulose chromatography papers (Sigma-Aldrich) attached to a support made of 0.8 mm and 2 mm thick acrylic glasses. Once the rotating disks are inserted into the humid enclosure containing wet papers, the rotary engine can start and run autonomously as long as papers remain wet. FIG. 13 shows components forming the device.

To characterize the oscillatory engine, the room can have RH and temperature maintained at 20% and 25° C., respectively. A water container made of acrylic classes can be placed on a ceramic top heater (Corning, PC-600D). The temperature of the water can be monitored with a digital thermometer (Deltatrak). The flow rate of the surrounding air can be maintained at ~0.06 m/s using a computer fan (Sunon) and a hot wire anemometer (Cole-Palmer, EW-30005-85) can be used to measure the air velocity. The oscillatory engine can be placed on top of the water surface inside the container. While the water temperature can be varied form 16° C. to 31° C., the oscillation frequency of shutters can be recorded using a digital camera (Canon EOS Rebel T5i). The compression applied to the buckling beam can be slightly adjusted to achieve the maximum oscillation rate for different water temperatures. Although HYDRAs prepared using 8 μm thick polyimide tapes showed better expansion and contraction ratio, in part due to bigger changes in curvature in the tapes, HYDRAs prepared using 25 μm thick polyimide tapes can also cause oscillations.

Thinner sheets can provide greater shape change due to the square dependence of bending modulus to the thickness of tapes.

To characterize the rotary engine, the five-disk rotary engine can be placed in a closed chamber of 2 mm thick acrylic glasses. A stream of humidity-controlled air can be pumped into the chamber through plastic tubing. RH and temperature can be measured both in the humid enclose of the rotary engine and in the surrounding environment. Humidity and temperature in the chamber can be measured using Vaisala HMP77 Humidity and Temperature Probe. Humidity inside the humid enclosure can be measured using Honeywell HIH-4021 along with a data acquisition card (NI-USB-6008). The temperature of the wet chromatography paper can be measured using a digital thermometer (Deltatrak). A small electric fan can be placed in the chamber to control airflow surrounding the rotary engine and the air velocity can be monitored using a hot wire anemometer (Cole-Palmer, EW-30005-85). The rotational speed can be recorded using a digital camera (Canon EOS Rebel T5i). The chromatography paper can be fully saturated with water.

For electricity generation, the RH and Temperature of the room can be maintained at 20% and 25° C., respectively. The speed of the air flow can be maintained at ~0.3 m/s (measured with a hot wire anemometer, Col-Palmer, EW-30005-85). The oscillatory engine, along with water container, can be placed on top of a ceramic heater (Corning®, PC-600D). The water temperature can be monitored using a digital thermometer and kept at 30° C. The internal spring load can be disconnected, and the HYDRAs can be connected to an electromagnetic generator with a short thread. The electromagnetic generator can include a stack of magnets rotating between two copper coils. Copper coils can be formed by winding a total of 22 Kfeet of 42 gauge magnet wire (Polytech Coil Winding, Tacoma, Wash., USA). The magnet stack can include two 2"×½"×¼" and two 2"×½"×⅛" neodymium magnets (K&J Magnetics). Silicon nitride ball bearings (VXB) can be used to allow magnets to rotate with respect to the coils. Two Light Emitting Diodes (LEDs, HLMP-K155, Avago Technologies) can be oppositely connected to the coils. The oscillatory engine can rotate the generator and provide power to light the LEDs repeatedly in alternating order. The voltage and power generation can be measured by replacing the LEDs with a resistor of 100 kΩ. The voltage across the resistor can be measured using a digital multimeter (34410A, Agilent) controlled by a Labview program.

Referring to FIGS. 1-3 for the purpose of illustration and not limitation, water confined to nanoscale cavities, conduits, and surfaces within hygroscopic materials can induce large pressures in respond to changing relative humidity (FIG. 1a). FIG. 1b shows a scanning electron microscopy image of the cross section of *B subtilis* spore. Spores can exhibit strong mechanical response to changing relative humidity by absorbing and releasing moisture. FIG. 1c shows a false-colored SEM picture of spores deposited on an 8-micrometer thick polyimide tape. The spore-coated films bend and straighten in response to changing relative humidity (FIG. 1d). Patterning equal spaced spore layers on both sides of the plastic tape can create linearly expanding and contracting structures (FIG. 1e). Stacking the tapes with air gaps between them can result in a material that can be scaled in two dimensions without compromising hydration/dehydration kinetics (1e,f). A shutter mechanism can create oscillations (2a). FIG. 2b shows a device that can exhibit self-starting oscillatory movement when placed above water. Rotary motion can lead to cyclical changes of relative humidity experienced by the spores (FIG. 3a). The increased curvature on the dry side can shift the center of mass of the entire structure away from the axis of rotation and can create torque. FIG. 3a shows a device whose continuous rotation can be powered by evaporation from the wet paper within the device.

Referring now to FIGS. 4 and 5, for the purpose of illustration and not limitation, HYDRAs are provided. FIGS. 4a,b show spore-coated polyimide tapes at low (FIG. 4a) and high (FIG. 4b) relative humidity. Patterning equally spaced spore layers on both sides of the plastic tape can create linearly expanding and contracting muscles (FIGS. 4 c,d). HYDRA strips can work in parallel to lift weights (FIGS. 5a,b). Elongation of individual strips as a function of relative humidity shows that HYDRAs can quadruple their length (FIG. 5c). The inset shows estimated radius of curvature of the arcs forming the HYDRAs. Markers indicate the average data values with error bars showing the standard deviation calculated for five measurements. The elongation of HYDRAs can reduce only slightly after one million cycles (FIG. 5d). The normalized length of a HYDRA strip in dry and humid conditions as a function of load weights is shown in FIG. 5e. Scale bars: FIG. 4a,b: 2 mm; FIGS. 4c,d and 5a,b: 2 cm; FIG. 5c,e: 1 cm.

Referring to FIGS. 6-8, for the purpose of illustration and not limitation, the oscillator can include horizontally placed HYDRAs coupled to a load spring and shutters that can control permeation of moisture. Shutters can be connected to a beam that is compressed between its buckling limit so that it has two stable configurations (FIG. 6a). As the beam switches its position due to the force exerted by HYDRAs, the shutters can open and close and alter the relative humidity of the chamber (FIG. 6b). FIG. 6c shows HYDRAs assembled in parallel pulling onto load springs. FIG. 6d shows the average period of oscillations as a function of water surface temperature. Markers indicate the average data values with error bars showing the standard deviation calculated from three measurements. FIG. 7 shows four stages of oscillatory motion: Stage I: when the shutters are closed, the relative humidity of the chamber can increase, causing HYRDAs to expand. Stage II: as HYDRAs expand toward the right, they can force the buckled beam to switch its position. Stage III: opening of the shutters can let the relative humidity of the chamber recede, causing HYDRAs to contract. The cycle can be completed when contracting HYDRAs pull the buckled beam and force it to switch back to the left configuration (stage IV), which can then close the shutters and bring the system back to stage I. FIG. 8a shows the oscillator connected to an electromagnetic generator (scale bar: 2 cm). The inset image shows the LED lit during operation. Voltage and power measured across a load resistor of 100 kΩ is shown in FIGS. 8b,c.

Figure 9D:
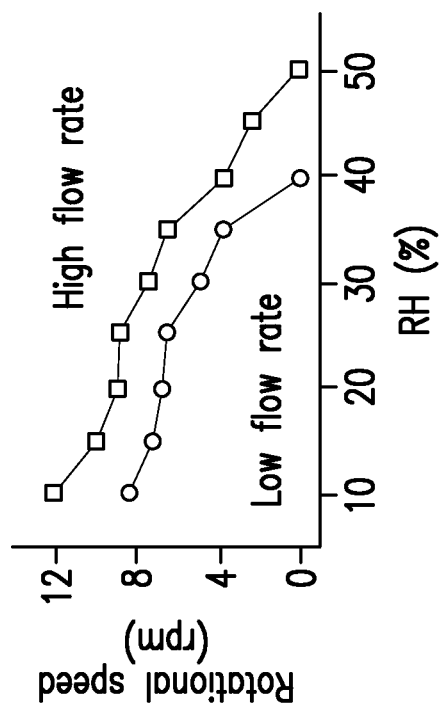
Figure 9C:
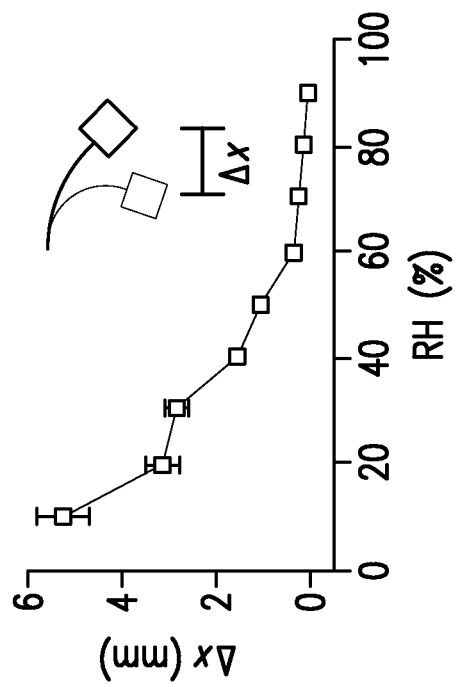

Referring to FIGS. 9 and 10 for the purpose of illustration and not limitation, a rotary engine is provided. FIG. 1a shows a side view of a rotary engine. Wet paper provides the humidity gradient. Plastic blocks weighing 15 mg attached to HYDRAs can increase the amount of mass shifting position relative to the axis of rotation. FIGS. 1b,c show images and measurements showing the horizontal shifts of the positions of plastic blocks attached to HYDRAs. Markers indicate the average data values with error bars showing the standard deviation calculated from measurements on five samples. FIG. 9d shows rotation speed measured as a function of external relative humidity and at two different airflow speeds near the device. The rotary engine can drive a vehicle forward if its rotation is coupled to the wheels.

FIG. 10 shows images of the position of a miniature car driven by a rotary engine. Scale bars: FIGS. 9a and 8: 2 cm; FIG. 9b: 5 mm.

FIG. 11 illustrates, for the purpose of illustration and not limitation, an example assembly process for long hygroscopy-driven artificial muscles in accordance with the disclosed subject matter. The process can include starting with a polyimide tape (FIG. 11a). A Poly-L-lysine coating can be disposed on portions of a first side of the tape with spaces in-between (FIG. 11b). A Poly-L-lysine coating can be disposed on portions of a second side of the tape with spaces in-between (FIG. 11c). For example, where there are spaces on the first side, there can be Poly-L-lysine on the second side, and vice versa. A spore/glue mixture coating can be disposed on the Poly-L-lysine coating on the first side (FIG. 11d). A spore/glue mixture coating can be disposed on the Poly-L-lysine coating on the second side (FIG. 11e). The hygroscopy-driven artificial muscle can then be allowed to dry (FIG. 11f).

FIG. 12 illustrates, for the purpose of illustration and not limitation, parts of an evaporation-driven engine for creation of linear motion in accordance with the disclosed subject matter. The engine can include floating components (FIG. 12a). The engine can include a structure including a hydrophobic coating (FIG. 12b). The structure can have a mechanical load, for example, load springs (FIG. 12c). HYDRAs can be disposed over the floating components, and a bar can be used to couple the HYDRAs to the shutters (FIG. 12d). Balsa wood shutters can be placed over the HYDRAs, such that the HYDRAs are disposed between the shutters and a water source (FIG. 12e). Compression screws can be used to adjust the compression applied to the buckle beam (FIG. 12f).

FIG. 13 illustrates, for the purpose of illustration and not limitation, parts of an evaporation-driven engine for creation of rotary motion in accordance with the disclosed subject matter. The engine can include several concentric rings having HYDRAs coupled to the circumference region of the rings (FIGS. 13a,b). The engine can also include a humidity chamber configured to enclose a portion of the disks (FIG. 13c, d). The humidity chamber can include a paper lining, which can be wetted by water. FIG. 13e shows the assembled evaporation-driven engine for creation of rotary motion.

The foregoing merely illustrates the principles of the disclosed subject matter. Various modification and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope.

The invention claimed is:

1. An evaporation-driven engine comprising:
   A water container having a shutter mechanism structurally connected to the water container and a water source having a high humidity zone proximate a surface of the water source;
   a supporting structure; and
   a hygroscopic material disposed on the supporting structure and configured to generate mechanical force in response to a changing relative humidity;
   wherein the hygroscopic material is repeatedly exposed to the high humidity zone and removed from high humidity zone thereby causing the hygroscopic material to generate mechanical force, and
   wherein the hygroscopic material is disposed alternately on a first side of the supporting structure and on a second side of the supporting structure.

2. The evaporation-driven engine of claim 1, wherein the hygroscopic material comprises bacterial spores.

3. The evaporation-driven engine of claim 2, wherein the bacterial spores are *Bacillus subtilis* spores.

4. The evaporation-driven engine of claim 1, wherein the supporting structure is a sheet.

5. The evaporation-driven engine of claim 4, wherein the sheet is a polyimide sheet.

6. The evaporation-driven engine of claim 4, wherein the hygroscopic material is disposed on a first side of the sheet.

7. The evaporation-driven engine of claim 1, further comprising a plurality of supporting structures, each supporting structure having a hygroscopic material disposed thereon.

8. The evaporation-driven engine of claim 1, wherein the hygroscopic material is repeatedly exposed to the high humidity zone and removed from high humidity zone by moving the hygroscopic material.

9. The evaporation-driven engine of claim 1, wherein a volume of the high humidity zone changes over time.

10. The evaporation-driven engine of claim 1, wherein the hygroscopic material is repeatedly exposed to the high humidity zone and removed from high humidity zone by varying the high humidity zone.

11. The evaporation-driven engine of claim 1, wherein the shutter mechanism is disposed between the surface of the water source and the hygroscopic material.

12. The evaporation-driven engine of claim 1, wherein the hygroscopic material is disposed between the surface of the water source and the shutter mechanism.

13. The evaporation-driven engine of claim 1, wherein the water source is a body of water.

14. An evaporation-driven engine for creation of linear motion, comprising:
   a water container having a water pool and a shutter mechanism structurally connected to the water container, the shutter mechanism moveable between an open configuration, in which the water container is open and a closed configuration, in which the water container is closed; and
   at least one hygroscopy driven artificial muscle (HYDRA) suspended above the water pool, each HYDRA having an extended position and a contracted position, and each HYDRA configured to transition from the extended position to the contracted position in relatively low humidity and transition from the contracted position to the extended position in relatively high humidity;
   wherein the HYDRA is functionally coupled to the shutter mechanism such that when the HYDRA transitions from the extended position to the contracted position, the HYDRA causes the shutter mechanism to close, and when the HYDRA transitions from the contracted position to the extended position, the HYDRA causes the shutter mechanism to open.

15. The evaporation-driven engine of claim 14, wherein each HYDRA comprises a support structure and a hygroscopic material disposed alternately on a first side of the support structure and on a second side of the support structure.

16. The evaporation-driven engine of claim 14, wherein the HYDRA comprises a plurality of HYDRAs.

17. The evaporation-driven engine of claim 14, further comprising a bistable element disposed between the at least one HYDRA and the shutter mechanism.

18. The evaporation-driven engine of claim 14, wherein the HYDRA is functionally coupled to an electromagnetic generator.

19. The evaporation-driven engine of claim 14, further comprising a protection layer disposed between the water and the HYDRA such that the HYDRA does not contact the water.

20. The evaporation-driven engine of claim 14, further comprising a mechanical load configured to hold the HYDRA in tension.

21. The evaporation-driven engine of claim 14, further comprising a floating element configured to float on the water and support the HYDRA.

22. The evaporation-driven engine of claim 14, wherein the shutter mechanism is disposed between the surface of the water source and the hygroscopic material.

23. The evaporation-driven engine of claim 14, wherein the hygroscopic material is disposed between the surface of the water source and the shutter mechanism.

24. The evaporation-driven engine of claim 14, wherein the water container has a bottom, the bottom being open, and wherein the water pool is a body of water.

25. An evaporation-driven engine for creation of rotary motion, comprising:
  at least one disk having a circumference region and a center;
  an axle disposed through the center of the disk such that the disk can rotate freely about the center;
  a plurality of hygroscopy driven artificial muscles (HYDRAs) each having a first end, a second end, each first end coupled to the circumference region of the disk such that the HYDRAs extend and contract radially relative the disk, each HYDRA having an extended position and a contracted position, and each HYDRA configured to transition from the extended position to the contracted position in relatively low humidity and transition from the contracted position to the extended position in relatively high humidity; and
  a humidity chamber configured to enclose a portion of the disk such that a first subset of the HYDRAs are disposed within the humidity chamber and are in the extended position, and a second subset of the HYDRAs are disposed outside the humidity chamber and are in the contracted position;
  wherein a center of mass of the disk is offset from the center of the disk due to the first subset of HYDRAs in the extended position and the second subset of HYDRAs in the contracted position, thereby causing a torque which creates rotational motion of the disk about the center and causes the first subset of HYDRAs that are disposed within the humidity chamber to rotate out of the humidity chamber and transition from the extended position to the contracted position, and the second subset of HYDRAs that are disposed outside the humidity chamber rotate into the humidity chamber and transition from the contracted position to the extended position thereby sustaining rotational motion.

26. The evaporation-driven engine of claim 25, wherein each HYDRA comprises a supporting structure and a hygroscopic material disposed on a first side of the supporting structure.

27. The evaporation-driven engine of claim 25, wherein the disk comprises a plurality of disks.

28. The evaporation-driven engine of claim 25, wherein the humidity chamber comprises a paper lining, the paper lining being wetted by water.

29. The evaporation-driven engine of claim 25, wherein the HYDRAs extend and contract radially outward from the disk.

30. The evaporation-driven engine of claim 25, wherein the HYDRAs extend and contract radially inward from the disk.

31. The evaporation-driven engine of claim 25, wherein each HYDRAs includes weight disposed on the second end.

* * * * *